US006340778B1

(12) United States Patent
Bueschken et al.

(10) Patent No.: US 6,340,778 B1
(45) Date of Patent: Jan. 22, 2002

(54) PROCESS FOR CATALYTIC ALDOL CONDENSATIONS BY MEANS OF A MULTIPHASE REACTION

(75) Inventors: Wilfried Bueschken; Klaus-Diether Wiese, both of Haltern; Guido Protzmann, Marl; Juergen Koch, Haltern, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/694,350

(22) Filed: Oct. 24, 2000

(30) Foreign Application Priority Data

Nov. 30, 1999 (DE) .......................................... 199 57 522

(51) Int. Cl.$^7$ ............................................... C07C 45/72
(52) U.S. Cl. ....................... 568/463; 568/461; 568/462; 568/463; 568/464; 568/881; 568/885; 562/531
(58) Field of Search ................................ 568/461, 462, 568/463, 464, 881, 885; 562/531

(56) References Cited

U.S. PATENT DOCUMENTS 5,254,743 A * 10/1993 Holmgren et al. .......... 568/463
5,840,992 A * 11/1998 Kido et al. .................. 568/392

FOREIGN PATENT DOCUMENTS

WO    WO 94/20034    10/1993

OTHER PUBLICATIONS

G. Duembgen D. Neubauer, Chemie–Ing.–Techn., 41, 974 (1969).
G.R. Muddarris, Hydrocarbon Processing, (1980), "Now, MTBE from Butane", pp. 91–95.

Heinz Brauer, Grundlagen der Einphasen–und Mehrphasenstroemungen, Verlag Sauerlaender, Aarau and Frankfurt am Main, (1971).
v.w. Weekman J., J.E. Myers: "Fluid–Flow Characteristics of Cocurrent Gas–Liquid Flow in Packed Beds", AIChE Journal, vol. 10 (No. 6), Nov. 1964, pp. 951–957.
R.P. Larkins, R. P. White, D.W. Jeffrey: "Two–Phase Cocurrent Flow in Packed Beds", AIChE Journal, vol. 7 (No. 2), Jun. 1961, pp. 231–239.
N. Midoux, M. Favier, J–C. Charpentier: "Flow Pattern, Pressure Loss and Liquid Holdup Data in Gas–Liquid Down–Flow Packed Beds with Foaming and Non–Foaming Liquids", J. Chem. Eng. of Japan, vol. 9 (No. 5), (1976) pp. 350–356.
D. Sweeney: "A Correlation for Pressure Drop in Two–Phase Concurrent Flow in Packed Beds", A1ChE Journal, vol. 13, Jul. 1967, pp. 663,669.
Y. Sato, T. Hirose, F. Takahashi, M. Toda: "Pressure Loss and Liquid Hold Up in Packed Bed Reactor with Cocurrent Gas–Liquid Down Flow", J. Chem. Eng. of Japan, vol. 6, (No. 2), 1973, pp. 147–152.
VDI–Waemeatlas, 7$^{th}$ augmented edition, VDI–Verlag GmbH, Duesseldorf 1994, sections Lal to Lgb7.

* cited by examiner

Primary Examiner—Sreeni Padmanabhan
(74) Attorney, Agent, or Firm—Oblon, Spivak, McClelland, Maier & Neustadt, P.C.

(57) ABSTRACT

The invention relates to a process for the catalytic aldol condensation of aldehydes by means of a multiphase reaction in a tube reactor, wherein the catalyst is present in the continuous phase and at least one aldehyde is present in a dispersed phase and the loading factor B of the tube reactor is equal to or greater than 0.8; the aldol condensation products obtained in this way can be used for preparing alcohols or carboxylic acids.

20 Claims, 1 Drawing Sheet

Fig. 1

PROCESS FOR CATALYTIC ALDOL CONDENSATIONS BY MEANS OF A MULTIPHASE REACTION

BACKGROUND OF THE INVENTION

1. Field of the Invention

The present invention relates to a process for carrying out multiphase reactions in a tube reactor, in particular for preparing α,β-unsaturated aldehydes by aldol condensation of aldehydes.

2. Discussion of the Related Art

Because of their reactivity, unsaturated aldehydes are starting materials for the preparation of many organic compounds. Their selective hydrogenation results in the corresponding saturated aldehydes which are also the basis of many syntheses. The oxidation of aldehydes leads to carboxylic acids which are utilized industrially. The hydrogenation of aldehydes leads to saturated alcohols which are used for preparing plasticizers and detergents.

The aldol reaction of n-butyraldehyde with simultaneous elimination of water to give 2-ethylhexenal is carried out worldwide on a large scale since the hydrogenation product, 2-ethylhexanol, is widely used as a plasticizer alcohol. A base dissolved in water is customarily employed as catalyst. Typically, use is made of aqueous sodium hydroxide solution having a NaOH content in the percentage range. The reaction is frequently carried out in a temperature range of 80–150° C., a pressure below 5 bar and a phase ratio of organic phase to catalyst phase of 1:20 (Hydrocarbon Processing, October 1980, Section 2, pages 93–102). This reaction can be performed, for example, in a stirred vessel (DE 19 06 850, DE 927 626), in a packed column operated in countercurrent (G. Dümbgen, D. Neubauer, Chemie-Ing.-Techn., 41, 974 (1969)), or in a flow tube (GB 761 203). All these processes give 2-ethylhexenal in a selectivity of up to 98% at conversions of 98.5%. A disadvantage is that at relatively high temperatures part of the n-butyraldehyde used is irreversibly lost as a result of the Cannizzaro reaction. The butyric acid formed in the Cannizzaro reaction neutralizes the basic catalyst. Part of the catalyst solution containing a high loading of organic material therefore has to be discharged continually and replaced by fresh catalyst.

Valeraldehyde can be reacted similarly to give 2-propylheptenal. The aldol condensation of the C$_5$-aldehydes can be carried out in stirred reactors which are equipped with internal heat exchangers to remove the heat. This reaction procedure is described, for example, in WO 93/20034 and is, because of the moving parts, susceptible to mechanical problems and in addition, is complicated in terms of construction and maintenance because of the heat exchangers built into the reactor.

In the case of aldehydes having more than 6 carbon atoms, the reaction rate is still lower because of the low solubility of the aldehydes in the aqueous catalyst phase and is therefore often no longer economical. It is likewise difficult to carry out the aldol condensation of branched aldehydes such as 3-methylbutanal.

The condensation of aldehydes can also be carried out in the homogeneous phase, e.g. using amines as a catalyst. These processes have the disadvantages that more by-products are formed and the catalyst has to be separated from the product mixture. For this reason, industrial aldol condensations are preferably carried out as multiphase reactions, in particular as two-phase reactions.

For the purposes of the following, two-phase reactions are reactions which occur with the participation of two fluid phases which are immiscible or only partially miscible. In the aldol condensation of aldehydes, two liquid phases which are immiscible or have a miscibility gap are present. At the beginning of the reaction, the two phases consist of the starting material and the catalyst solution, while after the reaction is complete they consist of the product and the catalyst phases.

In every two-phase reaction, the problem of mass transfer has to be overcome. The starting materials have to be transported into the catalyst phase and the products may have to be transported back. Since transport processes are frequently slower than the actual reaction, such reactions are determined by the rate of mass transfer, so the reaction is referred to as a mass-transfer-limited reaction.

In order to obtain industrially acceptable space-time yields in a multiphase reaction, particularly in one in which the phases are virtually insoluble in one another, the materials have to be brought into very intimate contact with one another. It is necessary to generate a mass transfer area a, between the phases which is as large as possible. On the other hand, the phases have to be able to be separated easily again after the reaction is complete. Excessive mixing can lead to difficulties here, since emulsions can be formed.

Apart from a high mass transfer area $a_s$, a very high mass transfer coefficient $k_1$ should be achieved in all multiphase reactions. Overall, the KLA value, i.e. the product of $k_1$ and $a_s$ in the mass transfer equation is:

$$j=k_1 a_s (C^*-C)$$

where j [mol/s]: the molar flow of reacting component through the phase interface (e.g. entry of aldehyde into the catalyst phase), $k_1$ [m/s]: mass transfer coefficient, $a_s$ [m$^2$]: phase interface area in the reactor (e.g. aldehyde in the catalyst phase), C* [mol/m$^3$]: maximum solubility of the starting material in the second phase and C [mol/m$^3$]: actual concentration of the starting material which in turn is coupled to the reaction rate, should be a maximum.

A further problem in multiphase reactions is the removal of heat in the case of an exothermic reaction. If the reaction rate is increased by improving the mass transfer, it is naturally also necessary to remove more heat which could lead to an undesirable temperature increase and even cause a runaway reaction.

For this reason, a two-phase aldol condensation is frequently carried out in a stirred reactor. However, in a stirred reactor, one has to accept the continual back-mixing which reduces the effective concentration of the reactants. This leads to a lowering of the space-time yield, which in turn has to be compensated for by an increased reaction volume.

Alternatively, the two-phase reaction could also be carried out in a flow tube. Here, however, there is the danger of the phases separations and the reaction rate decreasing to an excessive extent. Furthermore, the above-discussed problems of heat removal have to be taken into account.

SUMMARY OF THE INVENTION

It is therefore an object of the present invention to provide a process for carrying out multiphase reactions, which process is particularly suitable for carrying out aldol condensations.

In technical terms, the novel process should meet the following demands made of multiphase processes:

generation of high and stable mass transfer between the participating phases;

simplicity of implementation, if possible using customary industrial apparatuses;

simple and reliable heat removal;

high operating safety; and simple and reliable scale-up.

In respect of the intended preparation of ($\alpha,\beta$-unsaturated aldehydes by aldol condensation, the following specific requirements are added:

high selectivity, avoidance of, in particular, high-boiling by-products;

suppression of the Cannizzaro reaction, therefore no or only small catalyst discharge;

high space-time yield, small reactors; and high product purity.

The present invention accordingly provides a process for the catalytic aldol condensation of aldehydes by means of a multiphase reaction in a tube reactor, wherein the catalyst is present in a continuous phase and at least one aldehyde is present in a dispersed phase and the loading factor B of the reactor is equal to or greater than 0.8.

DESCRIPTION OF THE PREFERRED EMBODIMENTS

In the process of the invention, we have found a surprisingly simple process for carrying out two-phase reactions which can be carried out in a tube reactor, if desired containing packing or internal fittings, and is suitable for the aldol condensation of aldehydes to give unsaturated aldehydes in high space-time yield and with high selectivities.

In the process of the invention, the aldol condensation of an aldehyde with itself can be carried out, i.e. only one aldehyde is used. It is also possible to use a mixture of two or more aldehydes which may be present in different phases of the multiphase reaction.

If a mixture of two or more aldehydes is used, these aldehydes can have the same number or a different number of carbon atoms.

In each case, at least one aldehyde to be reacted has to be present in the dispersed phase. The process of the invention for aldol condensation enables aldehydes having from 1 to 15, preferably from 4 to 15, particularly preferably from 4 to 6, carbon atoms to be converted into the corresponding unsaturated aldehydes.

The tube reactor used in the process of the invention can contain packing or internal fittings. For the purposes of the present invention, examples of packing are: Raschig rings, saddles, Pall rings, tellerettes, wire mesh rings or woven wire mesh. Examples of internal fittings are filter plates, baffles, column trays, perforated plates or other mixing devices. However, for the purposes of the present invention, internal fittings can also comprise a plurality of narrow, parallel tubes to form a multitube reactor. Particular preference is given to structured mixer packings or demister packings.

In the process of the invention, it is also of critical importance to adhere to or exceed a minimum cross-sectional throughput or the loading factor B of the tube reactor. In upflow operation of the reactor (flow direction from the bottom to the top), the flooding point should be exceeded. The reactor is thus operated above the point at which bubble columns are usually operated. In downflow operation (flow direction from the top to the bottom), the cross-sectional throughput must be set so that the reactor is completely flooded. Thus, the process is operated above the point at which it would still be possible to speak of a trickle bed.

To fix the minimum necessary loading of the reactor more precisely, the loading factor B of the tube reactor is calculated as a dimensionless pressure drop $$B=PD/PS$$

where PD [Pa/m] is a pressure drop per unit length over the reactor under operating conditions and PS [Pa/m] is a mathematical parameter having the dimensions of a pressure per unit length, defined as the ratio of mass flow M [kg/s] of all components in the reactor to the volume flow V [m$^3$/s] of all components under operating conditions, multiplied by g=9.81 m/s$^2$, i.e. PS=(M/V)·g. To put it in concrete terms, PS would be the static pressure per meter of a multiphase mixture in an upright tube if all phases were to flow at the same velocity. PS is a purely mathematical parameter which is derived from the mass flows fed to the reactor and is independent of the flow direction in the reactor, the flow velocity of all phases or the flooding state of the reactor.

The pressure drop PD [Pa/m] is used as a mathematical parameter to fix the process conditions and can be calculated by established methods for single-phase or multiphase flows. Appropriate methods of calculating the pressure drop PD in tubes, internal fittings or packed beds, etc., may be found, for example, in the VDI-Wärmeatlas, 7th augmented edition, VDI-Verlag GmbH, Düsseldorf 1994, sections La1 to Lgb7, and also in the standard work by Heinz Brauer, Grundlagen der Einphasen- und Mehrphasenströmungen, Verlag Sauerländer, Aarau and Frankflurt am Main, 1971, which are incorporated herein by reference.

The pressure drop PD in the case of single-phase flow through an empty tube is given by:

$$PD=Cw·\rho/2·w^2/D$$

where

Cw: resistance coefficient of the tube through which flow occurs;

D [m]: tube diameter; and $\rho$ [kg/M$^3$]: density of the flowing medium under operating conditions; and w [m/s]: flow velocity=volume of flow/cross-sectional area.

In the case of flow through packing, beds or internal fittings, the velocity w is to be replaced by the effective velocity (w/$\psi$) and the tube diameter D is to be replaced by the hydraulic channel diameter $d_H$ of the packing or internal fittings, so that:

$$PD=Cw·\rho/2·(w/\psi)^2·1/d_H$$

where $d_H$ [m]: hydraulic channel diameter;

$\psi$: empty tube fraction; and $C_w$: resistance coefficient of the apparatus with filling through which flow occurs.

The packing-related data $d_H$ and $\psi$ are frequently part of the delivery specifications for packing. For a series of packings, data are given in the abovementioned VDI-Wärmeatlas.

The empty tube fraction $\psi$ can also be determined experimentally by, for example, measuring the volume of the reactor before and after filling with the packing. The hydraulic channel diameter can in turn be calculated, if it is not known, from the specific surface area F [m$^2$/m$^3$] of the packing or internal fittings (generally known or able to be determined experimentally) using the simple relationship:

$$d_H = 4\psi/F.$$

The resistance coefficient of tubes, internal fittings and packing is generally described as a function of the Reynolds number Re, which gives information about the flow state under the chosen conditions. In the case of packing, internal fittings, etc., the following relationship can almost always be employed:

$$C_w = K_1/Re^n + K_2/Re^m$$

where frequently employed exponents are n=1, m=0 (method of S. Ergun, Chem. Engng. Progr. 48, (1948), 89) or n=1, m=0.1 (method of Brauer et al.). $K_1$, $K_2$ are packing-related constants which are known from supply data or from the literature (examples may be found in the VDI-Wärmeatlas and in Brauer et al.). However, they can also be determined experimentally by passing a liquid through the tube reactor containing packing at various velocities and determining Cw as a function of Re from the known data and the measured pressure drop.

The dimensionless Reynolds number Re is defined as Re=w·($\rho/\eta$)·D for empty tubes or Re=(w/$\psi$)·($\rho/\eta$)·$d_H$ for tubes containing internal fittings or packing. In each case, $\eta$ [Pa·s] is the viscosity and $\rho$ [kg/m$^3$] is the density of the flowing medium.

In the case of two-phase flows (here liquid-liquid for aldehyde-catalyst solution), the pressure drop increases overproportionally. Usually, using the Lockhart-Martinelli method (discussed in Brauer et al., above), the pressure drop of the two-phase flow $P_{l1l2}$ is expressed in relation to the pressure drop of one of the two phases, for example to the pressure drop of the pure flowing liquid catalyst phase $P_{l1}$, and expressed in relation to the ratio of the pressure drop of the other phase $P_{l2}$ regarded as flowing alone.

To calculate pressure drops in two-phase flow, use is frequently made of the dimensionless pressures $\phi^2 = P_{l1l2}/P_{l1}$ and $X^2 - P_{l1}/P_{l2}$. The further relationship $\phi^2$=function ($X^2$) has frequently been examined. Examples may be found in the following literature references, which are incorporated herein by reference:

Y. Sato, T. Hirose, F. Takahashi, M. Toda: "Pressure Loss and Liquid Hold Up in Packed Bed Reactor with Cocurrent Gas-Liquid Down Flow", J. Chem. Eng. of Japan, Vol. 6 (No. 2), 1973, 147–152;

D. Sweeney: "A Correlation for Pressure Drop in Two-Phase Concurrent Flow in Packed Beds", AIChE Journal, Vol. 13, 711967, 663–669;

V. W. Weekman, J. E. Myers: "Fluid-Flow Characteristics of Cocurrent Gas-Liquid Flow in Packed Beds", AIChE Journal, Vol. 10 (No. 6), 11/1964, 951–957;

R. P. Larkins, R. P. White, D. W. Jeffrey: "Two-phase Cocurrent Flow in Packed Beds", AIChE Journal, Vol. 7 (No. 2), 6/1961, 231–239 or N. Midoux, M. Favier, J.-C. Charpentier: "Flow Pattern, Pressure Loss and Liquid Holdup Data in Gas-Liquid Down-flow Packed Beds with Foaming and Non-foaming Liquids"; J. Chem. Eng. Of Japan, Vol. 9 (No. 5), 1976, 350–356.

The relationship proposed by Midoux is frequently utilized for the calculation. For example:

$$\phi^2 = 1 + 1/X + 1.14 X^{0.54}$$

This so-called Lockart-Martinelli relationship is depicted in graphical form in many works; detailed discussions of it may be found in many textbooks on process engineering and publications, for example in Brauer et al.

The pressure drop of the two-phase flow $P_{l1l2}$ is then derived from the experimentally determined pressure drop, or the pressure drop estimated as described above, of the pure flowing liquid phase $P_{l1}$ using:

$$P_{l1l2} = \phi^2 \cdot P_{l1}.$$

In general, expressed as a function of the reactor length L [m]

$$PD = P_{l1l2}/L.$$

The pressure drop of a multiphase flow can thus be calculated by customary methods of chemical engineering. The same applies to the previously defined dimensionless pressure drop B, i.e. the loading factor of the multiphase reactor.

The magnitude of the dimensionless loading factor B is a necessary fundamental condition in the process of the invention; B should be greater than or equal to 0.8, preferably greater than or equal to 0.9 or particularly preferably greater than or equal to 1.

In the region where B is greater than or equal to 0.8, a reactor operated from the top downwards begins to flood. It may be expressly pointed out that when these conditions are adhered to, the advantages of the process of the invention are achieved even when the reactor is operated from the bottom upwards or in another direction.

Higher cross-sectional loadings of the reactor (B>>1), recognizable by the increasing differential pressure over the reactor, are possible at any time and even desirable as long as it the increasing space-time yields justify the similarly increasing energy consumption. An upper limit is therefore imposed only by practical considerations such as energy consumption or difficulty of separating the phases after the reaction is complete.

It can thus be seen that, apart from the volume flow of the individual phases or the empty tube velocity w=V(IID$^2$/4) derived therefrom, the physical dimensions of the reactor (length L, diameter D) and, in particular, the data for the packing used (hydraulic diameter $d_H$, empty tube fraction $\psi$) play an important role. With the aid of these parameters, the process can be matched without difficulty to a wide variety of requirements; it is only important to adhere to the condition B$\geq$0.8, preferably B$\geq$0.9 and particularly preferably B$\geq$1.

In the case of slow reaction, one will, for example, select a small hydraulic diameter of the packing or select a large specific surface area of the packing, so that the required conditions for B are achieved even at small flow velocities. In this way, sufficient residence times over the length of a sensibly dimensioned industrial reactor are obtained. In the case of very fast reactions, a converse procedure is advisable.

A further criterion in carrying out the process of the invention is the ratio of the mass flow of the liquid, catalyst-containing phase $M_1$ to the mass flow of the disperse phases $M_2$. In the process of the invention for carrying out aldol condensations, the mass flow of the catalyst phase $M_1$ is greater than the mass flow $M_2$ of the disperse phase or phases. In the process of the invention, the mass ratio $M_1/M_2$ of the continuous phase ($M_1$) to the disperse phase(s) ($M_2$) can be greater than 2; it is preferred that $M_1/M_2>10$. Flow ratios of $M_1/M_2>100$ are quite possible and frequently even advantageous. Under the condition $M_1/M_2>2$, the catalyst phase is the continuous phase, while the disperse phase or phases is/are divided into fine droplets.

The process of the invention is frequently carried out in such a way that at least one phase, which contains an aldehyde, is dispersed, by means of the energy introduced into the tube reactor, in the continuous phase.

The size of the droplets obtained in this way can be estimated by means of customary engineering methods. Suitable methods employ relationships involving dimensionless parameters, for example:

$$d_s/d_H = k \cdot Re_{l1l2}^m \cdot We_{l1l2}^n$$

where ds: droplet diameter obtained by the Sauter method (described in Brauer et al.);

$d_H$: hydraulic diameter of the packing;

$Re_{l1l2}$: Reynolds number of the multiphase flow=$w_{l1l2} \cdot (\rho_{l1}/\eta_{l1}) \cdot (d_H/\psi)$;

$We_{l1l2}$: Weber number of the multiphase flow=$w_{l1l2}^2 \cdot (\rho_{l1}/\sigma_{l1l2}) \cdot (d_H/\psi)^2$;

k, m, n: empirical constants (known or determined by experiment);

w: empty tube velocity [m/s]=$V/(\Pi D^2/4)$;

V: volume flow under operating conditions [m$^3$/s];

$\rho$: density under operating conditions [kg/m$^3$];

$\eta$: viscosity under operating conditions [Pa·s]; and $\gamma$: interfacial tension under operating conditions [N/m]

and the indices l1 (first liquid phase) and l2 (second liquid phase).

In the case of structured packings such as Sulzer SMV or narrow tubes as internal fittings, it seem plausible that a calculated droplet diameter $d_s$ greater than the channel diameter is not sensible. However, this does not apply to permeable packings and packing elements such as wire mesh rings or woven wire mesh (known as demister packings or droplet precipitators). In the process of the invention, it is possible to use calculated droplet diameters which are at least equal to or smaller than the hydraulic channel diameter:

$$d_s/d_H \leq 1, \text{ preferably} < 0.9.$$

The calculated droplet diameter finally allows a mass transfer area to be calculated in accordance with $$A_s = 6\phi_{l2} d_s [m^2/m^3].$$

For the phase fraction $\phi_{l2}$ of the disperse phase (in the case of the aldol condensation, an organic phase containing at least one aldehyde is dispersed), the ratio of the empty tube velocities of the phases can be used:

$$\phi_{l2} \sim w_{l2}/w_{l\frac{1}{2}}.$$

The residence time $\tau$ of the phases flowing through the reactor can be calculated approximately as $\tau \sim L \cdot \phi/w_{l\frac{1}{2}}$. The residence time $\tau$ in the process of the invention is generally much less than one hour and can be in the minute range or even lower. Nevertheless, this completely unusual method of operation (high catalyst throughput in the reactor, comparatively low proportion of starting material in the reaction composition, and as a result a very short residence time) surprisingly achieves high space-time yields. Alternatively, at the same space-time yields it is possible to work at significantly lower temperatures than is customary, since the increase in the reaction rate, which can, for example, result in minimization of secondary reactions and thus improve selectivity, makes this economically feasible.

The process of the invention can be matched very flexibly to a wide variety of requirements. For specific requirements, the following embodiments of the process of the invention are possible:

If the application requires a very long mixing zone or calming zones are required, for example for decreasing mass flows, a cascaded arrangement of tube reactors having internal fittings or packing can be employed.

A cascaded arrangement of tube reactors or the alternative arrangement of packed and empty tube sections is advisable if a particularly low pressure drop is desired.

Furthermore, parallel arrangement of tube reactors or the use of a multitube reactor, in which the tubes can assume the function of internal fittings, can be used.

The heat removal in the case of strongly exothermic reactions, for example as in the aldol condensation, is also not critical in the process of the invention. The high throughput of the catalyst circuit acts as heat exchange medium so that, even in the case of adiabatic operation of the reactor, only small temperature differences arise and a homogeneous temperature distribution in the reactor without temperature peaks results. The heat generated can then conveniently be removed or exploited for energy recovery by means of any conventional heat exchanger located in the external catalyst circuit. To improve removal of heat, it can sometimes be useful to run the catalyst circuit at a higher circulation rate (i.e. at a higher B value) than is technically necessary, since the catalyst circuit enables a smaller temperature gradient over the reactor to be set.

Compared with the prior art, the process of the invention offers considerable advantages, for example:

high space-time yields can be achieved at comparatively low temperatures;

the formation of by-products is extremely low; and the process is gentle on the catalyst and it suffers from very little deactivation;

continuous discharge is minimized.

In the preparation according to the invention of α,β-unsaturated aldehydes by aldol condensation of aldehydes, a further advantage is that, owing to the high reaction rate, even aldehydes having a very low solubility in the catalyst phase can be converted economically into the corresponding aldol condensation products.

Suitable solvents for the preparation of the catalyst solution or phase are solvents which meet the following conditions:

the solvent is at most only slightly soluble in the product phase;

the product is only slightly soluble in the catalyst phase, containing the catalyst and solvent; and the solvent has a sufficiently high solvent capability for the catalyst used.

The continuous phase in the process of the invention (i.e. the catalyst phase) can consist substantially of water. The term "substantially" is used to mean that an additional solvent may be present in an amount of up to 5% by weight.

If desired, the catalyst phase can contain a phase transfer reagent, a surface-active or amphiphilic reagent or a surfactant.

In a particular embodiment the continuous phase can consist entirely of water. Furthermore, the continuous phase can consist largely of water and a water-soluble solvent. Organic solvents soluble in water which can be used are, for example, propanediol, glycerol, diethylene glycol (DEG) or dimethylformamide. The proportion of water and organic solvent preferably makes up more than 60% by weight, particularly preferably more than 80% by weight, of the phase.

As catalyst in the process of the invention, it is possible to use water-soluble, basic compounds such as hydroxides, hydrogencarbonates, carbonates, carboxylates or mixtures thereof in the form of their alkali metal or alkaline earth metal compounds. Preference is given to using alkali metal hydroxides such as sodium hydroxide.

The concentration of the catalyst in the continuous phase is from 0.1 to 15% by weight, in particular from 0.1 to 5% by weight.

The process of the invention is suitable for the reaction of aldehydes or aldehyde mixtures which can undergo condensation reactions. If only one aldehyde is used, the aldehyde has to have two α-hydrogen atom, on the same carbon atom, next to the CO group. If two or more different aldehydes are used, at least one of the aldehydes has to have two α-hydrogen atoms on the same carbon atom.

Aldehydes having two α-hydrogen atoms in accordance with the above definition are, for example, acetaldehyde, propanal, n-butyraldehyde, n-valeraldehyde, 3-methylbutyraldehyde, n-hexanal, 3-methylpentanal, 4-methylpentanal, n-heptanal, n-octanal, n-nonanal, n-decanal. These are also suitable for a homocondensation.

Examples of aldehydes having one α-hydrogen atom in accordance with the above definition are: isobutyraldehyde, 2-methylbutyraldehyde, 2-methylpentanal, 2-ethylhexanal, cyclohexyl aldehyde. Examples of aldehydes having no α-hydrogen atom are: benzaldehyde, 2,2-dimethylpropanal and formaldehyde. The aldehydes of the latter two groups can only undergo an aldol condensation with an aldehyde having two α-hydrogen atoms.

Preferred starting materials for the process of the invention are: n-butyraldehyde, n-valeraldehyde, a mixture of n-butyraldehyde and isobutyraldehyde, mixtures of n-valeraldehyde with 2-methylbutyraldehyde or 3-methylbutyraldehyde or the corresponding three-component mixture. It is likewise possible to use a mixture of $C_4$- and $C_5$-aldehydes or a mixture of the isomeric nonanals ($C_9$-aldehydes). These aldehydes can be prepared, for example by hydroformylation of olefins.

When using more than one aldehyde or an aldehyde mixture, the individual components can be fed separately into the stream of catalyst solution. It is likewise possible to mix all starting materials prior to feeding and to feed them into the reactor together. Furthermore, the aldehydes can be used as a solution. Solvents which can be used are inert liquids which are at most only slightly soluble in the catalyst solution, for example hydrocarbons (pentane, cyclohexane, toluene).

The present invention further provides for the use of the aldol condensation products prepared by the process of the invention. These can be used for the preparation of saturated alcohols by hydrogenation. The saturated alcohols obtained in this way can in turn be employed for the preparation of plasticizers, detergents or solvents. As precursors for plasticizer alcohols particular mention may be made of the unsaturated $C_8$- and $C_{10}$-aldehydes.

Furthermore, the aldol condensation products can be converted by selective hydrogenation into the saturated aldehydes and these can be converted into carboxylic acids by subsequent oxidation, i.e. they can be used for preparing carboxylic acids.

In addition, the unsaturated aldehydes are used in many syntheses because of their reactivity. A further field of application for the saturated and unsaturated aldehydes is their use as fragrances.

The process of the invention for the aldol condensation of aldehydes can be carried out in a temperature range of from 30° C. to 200° C., preferably in the range from 60° C. to 150° C.

The phases can flow through the reaction tube concurrently from the top to the bottom or vice versa. For safety reasons, preference is given to feeding the phases in from the top of the reactor.

The heat of reaction can be removed via various heat exchangers. The heat exchangers do not have to be in the vicinity of the reaction space, but can also, if desired, be located outside the reactor. The individual heat flows are dependent on the specific heat of reaction and on the desired temperatures in the reactor and in the work-up equipment.

The heat of reaction which has been removed can thus be utilized very simply, e.g. in the process itself, for heating a distillation apparatus or for generating steam.

The liquid mixture leaving the reactor is mechanically separated in a liquid-liquid separation vessel into the catalyst phase and the product phase. This can be carried out in settling vessels of various construction types or in centrifuges. For cost reasons, preference is given to settling vessels.

Although the residence times in the separation apparatus are not critical per se, they are preferably kept short. This has the following advantages: the separation apparatus is small and its capital cost is correspondingly low. When residence times are short, virtually no secondary reactions occur in the separation vessel. For the separation of the phases to occur quickly, the density difference between the two phases has to be sufficiently large and their viscosity has to be low. All three parameters are a function of the temperature and can easily be determined by initial experiments.

In addition, the density and viscosity of the catalyst solution can be varied by choice of the solvent and the catalyst concentration. A further possibility is to alter the density and viscosity of the product phase by addition of a solvent. Phase separation can be carried out in a wide temperature range. Here, the separation temperature can also be higher than the temperature of the reaction product at the outlet from the reactor. However, for energy reasons, it is disadvantageous to employ a higher temperature than the liquid temperature at the reactor outlet. The lowest possible temperature may be regarded as the pour point of one of the two liquid phases. However, in order to achieve short separation times, excessively low temperatures are avoided, as mentioned above.

The water of reaction formed dilutes the catalyst solution and therefore has to be continually removed from the process. This can be carried out by distillation of the output from the reactor, giving a water-containing azeotrope. This can in turn be separated into an aqueous phase and an organic phase. Part of the aqueous phase can be discharged to maintain the water balance. Excess water can also be removed from the separated catalyst phase by distillation. In addition, water of reaction can be removed by taking off part of the catalyst solution.

The product stream can, after separation, be purified by known methods, e.g. by distillation.

The catalyst solution which has been separated off is, if desired after discharge of a small proportion and correspondingly replacement by fresh catalyst solution, returned to the reactor.

Figure 1:
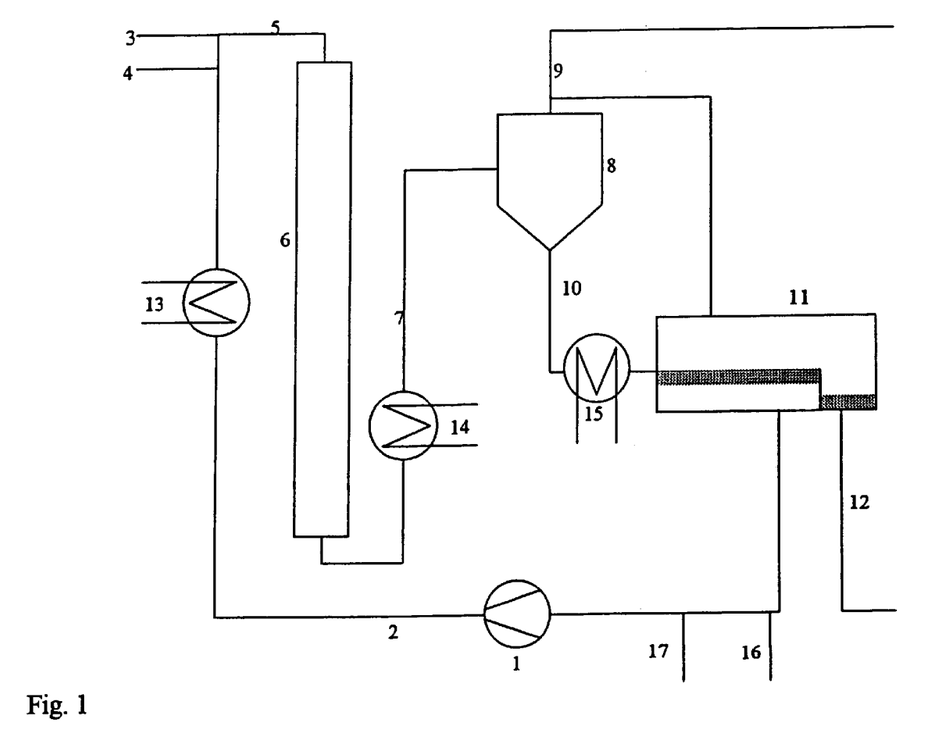
The FIGURE shows an experimental apparatus used to carry out the aldol condensation of aldehydes by the process in accordance with the present invention.

The aldol condensation of aldehydes by the process of the invention was carried out in an experimental apparatus which is shown schematically in FIG. 1. In this set-up, the continuous catalyst phase 2 is circulated by means of a pump 1. The aldehyde or the aldehyde mixture is mixed into the catalyst via line 3 or, in the case of separate introduction of different aldehydes, via the lines 3 and 4. In the examples described below, the starting materials were mixed in exclusively via line 3. The multiphase mixture obtained in this way was, in Examples 3 to 14, pumped via line 5 through a tube reactor 6 which had a length of 3 m and a diameter of 17.3 mm and was provided with static mixing elements having a hydraulic diameter of 2 mm. In Examples 1 and 2, use was made of other reactors whose dimensions are given in those examples. The resulting mixture, comprising the reaction product, unreacted starting material and the catalyst, was passed via line 7 to the optional gas separator 8 where it was freed of volatile constituents which were discharged via line 9. In the examples described below, with the exception of Example 2, this line was closed.

The liquid stream 10 obtained after the degassing step 8 was conveyed to a phase separation vessel 11. Here, the aqueous phase was separated off via line 2 and returned to the circuit. The organic phase which contains the reaction product and runs over a weir can be taken off via line 12.

The heat of reaction was removed by means of the heat exchangers 13, 14 and 15 located outside the reactor.

As solvent for the catalyst use was water or a mixture of water and diethylene glycol (DEG). The pairs of experiments 3 and 4, 5 and 6, 7 and 8, 9 and 10, 11 and 12 and 13 and 14 clearly shows the increase in conversion when using a solvent mixture.

The tables in Examples 3 to 14 show the catalyst composition in per cent by mass, the amount of aldehyde fed in and its composition in per cent by area derived from gas-chromatographic analysis.

The lower part of the second table of each example lists the product composition, also in per cent by area derived from gas-chromatographic analysis. In the documentation of Examples 3–14, no distinction has been made between the isomers of the individual $C_5$-acids or $C_5$-alcohols in the interest of simplicity. These values are summarized as "alcohol" or "acid". Likewise, the saturated 3-hydroxyalkanals of the $C_5$-aldehydes are summarized as "aldol addition compounds". The "trimers" represent the proportion of high boilers formed by aldol reaction (addition and condensation) of three $C_5$-aldehydes.

The upper part of the second table in each of the examples reports the space-time yield (STY), the conversion (C) of the aldehydes, the selectivity (S) to the desired aldol condensation products and the loading factor (B) of the tube reactor. In the catalyst composition given, it should be noted that these are initial values in Examples 3 to 14. The proportion of NaOH and, if present, DEG was slightly diluted by the water of reaction from the aldol condensation. In addition, the Cannizzaro reaction which proceeds in parallel to the aldol condensation leads to neutralization of the alkaline catalyst. Both effects are, however, so slight in the period of time for which the reaction was observed for this to be inconsequential for the description of the experiments and the experimental results.

Having generally described this invention, a further understanding can be obtained by reference to certain specific examples which are provided herein for purposes of illustration only and are not intended to be limiting unless otherwise specified.

The priority document, German patent application 19957522.3, filed Nov. 30, 1999, is incorporated herein by reference in its entirety.

EXAMPLES

Example 1 (Comparative Example)
Preparation of Propylheptenal From n-pentanal

Propylheptenal was prepared by condensation of n-pentanal in a flow tube. The reactor design, the phase ratio of organic phase to aqueous catalyst phase and the residence time were selected on the basis of an industrial-scale process for preparing 2-ethylhex-2-enal. The reactor of the above-described experimental plant (FIG. 1) was replaced by a 60 m long DN20 tube. The reactor volume was 19 l. (In a preliminary experiment not described here it had been ensured that an industrial-scale process for preparing 2-ethylhex-2-enal can be simulated well using this reactor).

The catalyst circulation was 500 l/h (2.7% strength aqueous NaOH). n-Pentanal was fed in at a volume flow of 50 l/h.

In continuous operation, the following results were obtained:

|  | Example 1a | Example 1b |
| --- | --- | --- |
| Temperature | 95° C. | 130° C. |
| Pressure | 1.0 bar | 2.7 bar |
| n-Pentanal | 24.0 mol % | 3.0 mol % |
| 2-Propylheptenal | 69.5 mol % | 94.4 mol $ |
| Remainder (mainly high boilers) | 6.5 mol % | 2.6 mol % |
| Space-time yield (STY) | 1.3 t/m$^3$/h | 1.8 t/m$^3$/h |

The loading factor B was 0.02.

Example 2
Preparation of 2-propylheptenal

The reactor used was a 995 mm long DN15 tube (internal diameter: 17.9 mm). The reactor was packed with wire mesh rings (Vereinigte Fülkörperfabriken, VFF, 4×4 mm with web, surface area: about 2100 m$^2$/m$^3$) as are used for distillation. A proportion of packing elements of 8.5% of the reactor volume was determined experimentally. The empty tube fraction was thus 91.5%, which corresponded to a free reactor volume of 229 cm$^3$. The effective hydraulic diameter was calculated as $d_H$=1.913 mm.

During the continuous experiment, the NaOH content of the catalyst solution was maintained at 2.85% by weight by addition of 1 molar sodium hydroxide solution.

The catalyst circulation was 400 l/h and n-pentanal was fed in at a volume flow of 1.0 l/h. To make the system inert, a small amount of nitrogen (0.5 mol/h) was additionally metered in.

The nitrogen present in the crude product leaves the gas separator 8 via line 9 together with an azeotrope containing water, n-pentanal and the products. The stream was cooled (cooler and separator are not shown in FIG. 1). At the separator an organic phase and an aqueous phase were formed. The organic phase was passed to the product separator 11. The aqueous phase was discarded.

The experiment was carried out at 1 bar and 95° C. The loading factor B was 9.92.

At equilibrium, a product having the following average composition was obtained:

|  | Starting material | Product |
| --- | --- | --- |
| n-Pentanal | 97.7 mol % | 7.7 mol % |
| Propylheptenal |  | 89.8 mol % |
| Remainder (mainly high boilers) | 2.3 mol % | 2.5 mol % |

The space-time yield was calculated as 2.6 t/m$^3$/h.

This experiment showed that even at 95° C. in a tube only 1 m long a high conversion with low formation of high boilers is achieved. The process of the invention gave higher space-time yields than a conventional process (Comparative Example 1).

Example 3

This example describes the process of the invention for the aldol condensation of n-pentanal to 2-propylheptenal (1+1 product). 400 kg/h of catalyst were passed through the reactor at a temperature of 110° C. at the autogenous pressure of the reactants. The reactor used was a 3 m long ND15 tube (internal diameter: 17.3 mm). The reactor was packed with packing elements from Sulzer having a hydraulic diameter of 2 mm (SMV 2).

| Catalyst | |
| --- | --- |
| NaOH | 2.34% by weight |
| Water | 97.66% by weight |
| Starting material flow [l/h] | 4.11 |
| Starting material composition | |
| n-Pentanal | 96.1% by weight |
| Aldols | 0.9% by weight |
| Trimers | 1.4% by weight |
| Remainder | 1.6% by weight |

The following result was achieved:

| | |
| --- | --- |
| STY [t/m$^3$/h] | 3.9 |
| Conversion | 97.6% |
| Selectivity | 96.2% |
| B | 15.34 |
| n-Pentanal (unreacted n-pentanal) | 2.3% by weight |
| 2-Propylheptenal | 94.0% by weight |
| Aldol addition products | 0.7% by weight |
| Trimers | 1.0% by weight |
| Remainder | 2.0% by weight |

Example 4

This example describes the process of the invention for the aldol condensation of n-pentanal to 2-propylheptenal (1+1 product) using the cosolvent diethylene glycol (DEG). 400 kg/h of catalyst were passed through the reactor (as described in Example 3) at a temperature of 110° C. at the autogenous pressure of the reactants.

| Catalyst | |
| --- | --- |
| NaOH | 3.76% by weight |
| Diethylene glycol | 50.00% by weight |
| Water | 46.24% by weight |
| Starting material flow [l/h] | 4.02 |
| Starting material composition | |
| n-Pentanal | 96.1% by weight |
| Aldols | 1.3% by weight |
| Trimers | 0.8% by weight |
| Remainder | 1.7% by weight |

The following result was achieved:

| | |
| --- | --- |
| STY [t/m$^3$/h] | 3.9 |
| Conversion | 99.5% |
| Selectivity | 95.9% |
| B | 13.91 |
| n-Pentanal (unreacted n-pentanal) | 0.5% by weight |
| 2-Propylheptenal | 95.4% by weight |
| Aldol addition products | 0.1% by weight |
| Trimers | 3.0% by weight |
| Remainder | 0.9% by weight |

Example 5

This example describes the process of the invention for the aldol condensation of 3-methylbutanal (3-MBA) to 2-isopropyl-5-methylhexenal (3+3). 400 kg/h of catalyst were passed through the reactor (as described in Example 3) at a temperature of 110° C. at the autogenous pressure of the reactants.

| Catalyst | |
| --- | --- |
| NaOH | 2.44% by weight |
| Water | 97.56% by weight |
| Starting material flow [l/h] | 4.27 |
| Starting material composition | |
| 3-Methylbutanal | 98.7% by weight |
| Aldols | 0.2% by weight |
| Trimers | 0.1% by weight |
| Remainder | 0.1% by weight |

The following result was achieved:

| | |
| --- | --- |
| STY [t/m$^3$/h] | 3.2 |
| Conversion | 78.2% |
| Selectivity | 93.3% |
| B | 15.48 |
| 3-Methylbutanal | 21.6% by weight |
| Alcohol | 1.2% by weight |
| 2-Isopropyl-5-methylhexenal | 72.0% by weight |
| Aldol additional products | 1.1% by weight |
| Trimers | 1.5% by weight |
| Remainder | 2.6% by weight |

Example 6

This example describes the process of the invention for the aldol condensation of 3-methylbutanal (3-MBA) to 2-isopropyl-5-methylhexenal (3+3) using the cosolvent diethylene glycol (DEG). 400 kg/h of catalyst were passed through the reactor (as described in Example 3) at a temperature of 110° C. at the autogenous pressure of the reactants.

| Catalyst | |
| --- | --- |
| NaOH | 3.46% by weight |
| Diethylene glycol | 50.00% by weight |
| Water | 46.54% |
| Starting material flow [l/h] | 4.00 |

-continued

| Starting material composition | |
|---|---|
| 3-Methylbutanal | 98.9% by weight |
| Aldol addition products | 0.2% by weight |
| Trimers | 0.1% by weight |
| Remainder | 0.8% by weight |

The following result was achieved:

| STY [t/m³/h] | 3.7 |
|---|---|
| Conversion | 95.7% |
| Selectivity | 95.2% |
| B | 13.91 |
| 3-Methylbutanal | 4.2% by weight |
| Alcohol | 0.5% by weight |
| 2-Isopropyl-5-methylhexenal | 90.1% by weight |
| Trimers | 2.6% by weight |
| Remainder | 2.6% by weight |

Example 7

This example describes the process of the invention for the co-aldol condensation of n-pentanal and 2-methylbutanal (2-MBA) to give an isodecenal consisting of the isomers 2-propyl-4-methylhexenal (1+2) and 2-propylheptenal (1+1). 400 kg/h of catalyst were passed through the reactor (as described in Example 3) at a temperature of 110° C. at the autogenous pressure of the reactants.

| Catalyst | |
|---|---|
| NaOH | 2.27% by weight |
| Water | 97.73% |
| Starting material flow [l/h] | 4.17 |
| Starting material composition | |
| 2-Methylbutanal | 51.3% by weight |
| n-Pentanal | 46.0% by weight |
| Acid | 0.3% by weight |
| Aldols | 0.9% by weight |
| Trimers | 0.1% by weight |
| Remainder | 1.3% by weight |

The following result was achieved:

| STY [t/m³/h] | 2.3 |
|---|---|
| Conversion | 57.7% |
| Selectivity | 94.8% |
| B | 15.40 |
| 2-Methylbutanal | 33.0% by weight |
| n-Pentanal | 3.1% by weight |
| Alcohol | 0.3% by weight |
| Acid | 1.2% by weight |
| 2-Propyl-4-methylhexenal | 24.4% by weight |
| 2-Propylheptenal | 34.3% by weight |
| Aldol addition products | 1.4 |
| Trimers | 1.1 |
| Remainder | 1.4 |

Example 8

This example describes the process of the invention for the co-aldol condensation of n-pentanal and 2-methylbutanal (2-MBA) to give an isodecenal consisting of the isomers 2-propyl-4-methylhexenal (1+2) and -propylheptenal (1+1) using the cosolvent diethylene glycol (DEG). 400 kg/h of catalyst were passed through the reactor (as described in Example 3) at a temperature of 110° at the autogenous pressure of the reactants.

| Catalyst | |
|---|---|
| NaOH | 3.25% by weight |
| Diethylene glycol | 45.00% by weight |
| Water | 51.75% |
| Starting material flow [l/h] | 3.66 |
| Starting material composition | |
| 2-Methylbutanal | 45.4% by weight |
| n-Pentanal | 51.2% by weight |
| Acid | 0.4% by weight |
| Aldols | 1.0% by weight |
| Trimers | 0.1% by weight |
| Remainder | 1.8% by weight |

The following result was achieved:

| STY [t/m³/h] | 2.7 |
|---|---|
| Conversion | 77.0% |
| Selectivity | 94.9% |
| B | 13.75 |
| 2-Methylbutanal | 18.4% by weight |
| n-Pentanal | 0.3% by weight |
| Alcohol | 0.8% by weight |
| Acid | 0.9% by weight |
| 2-Propyl-4-methylhexenal | 45.2% by weight |
| 2-Propylheptenal | 28.5% by weight |
| Aldol addition products | 0.9% by weight |
| Trimers | 4.1% by weight |
| Remainder | 1.2% by weight |

Example 9

This example describes the process of the invention for the co-aldol condensation of n-pentenal and 3-methylbutanal (3-MBA) to give an isodecenal consisting of the isomers 2-propyl-5-methylhexenal and 2-isopropylheptenal (1+3) and also 2-propylheptenal (1+1). 400 kg/h of catalyst were passed through the reactor (as described in Example 3) at a temperature of 110° C. at the autogenous pressure of the reactants.

| Catalyst | |
|---|---|
| NaOH | 2.13% by weight |
| Water | 97.87% |
| Starting material flow [l/h] | 4.14 |
| Starting material composition | |
| 2-Methylbutanal | 45.8% by weight |
| n-Pentanal | 52.4% by weight |
| Acid | 0.3% by weight |
| Aldols | 0.9% by weight |
| Trimers | 0.1% by weight |
| Remainder | 0.5% by weight |

The following result was achieved:

| | |
|---|---|
| STY [t/m³/h] | 3.7 |
| Conversion | 88.6% |
| Selectivity | 98.3% |
| B | 15.38 |
| 3-Methylbutanal | 7.7% by weight |
| n-Pentanal | 1.4% by weight |
| Acid | 0.3% by weight |
| 2-Propyl-5-methylhexenal | 12.6% by weight |
| 2-Isopropylheptenal | 51.8% by weight |
| 2-Propylheptenal | 22.4% by weight |
| Aldol addition products | 1.4% by weight |
| Trimers | 1.8% by weight |
| Remainder | 0.7% by weight |

Example 10

This example describes the process of the invention for the co-aldol condensation of n-pentanal and 3-methylbutanal (3-MBA) to give an isodecenal consisting of the isomers 2-propyl-5-methylhexenal and 2-isopropylheptenal (1+3) and also 2-propylheptenal (1+1) using the cosolvent diethylene glycol (DEG). 400kg/h of catalyst were passed through the reactor (as described in Example 3) at a temperature of 110° C. at the autogenous pressure of the reactants.

| Catalyst | |
|---|---|
| NaOH | 3.52% by weight |
| Diethylene glycol | 50.00% by weight |
| Water | 46.48% by weight |
| Starting material flow [l/h] | 4.21 |
| Starting material composition | |
| 3-Methylbutanal | 51.7% by weight |
| n-Pentanal | 45.7% by weight |
| Acid | 0.7% by weight |
| Aldols | 1.0% by weight |
| Trimers | 0.1% by weight |
| Remainder | 0.9% by weight |

The following result was achieved:

| | |
|---|---|
| STY [t/m³/h] | 4.1 |
| Conversion | 97.5% |
| Selectivity | 97.6% |
| B | 14.09 |
| 3-Methylbutanal | 1.8% by weight |
| n-Pentanal | 0.1% by weight |
| Alcohol | 0.1% by weight |
| Acid | 0.1% by weight |
| 2-Propyl-5-methylhexenal | 20.5% by weight |
| 2-Isopropylheptenal | 55.1% by weight |
| 2-Propylheptenal | 18.1% by weight |
| Aldol addition products | 1.2% by weight |
| Trimers | 2.1% by weight |
| Remainder | 0.9% by weight |

Example 11

This example describes the process of the invention for the co-aldol condensation of 2-MBA and 3-MBA to give an isodecenal consisting of the isomers 2-isopropyl-4-methylhexenal (2+3) and 2-isopropyl-5-methylhexenal (3+3). 400 kg/h of catalyst were passed through the reactor (as described in Example 3) at a temperature of 110° C. at the autogenous pressure of the reactants.

| Catalyst | |
|---|---|
| NaOH | 2.51% by weight |
| Water | 97.49% |
| Starting material flow [l/h] | 4.39 |
| Starting material composition | |
| 3-Methylbutanal | 48.0% by weight |
| 2-Methylbutanal | 47.5% by weight |
| Acid | 3.6% by weight |
| Aldols | 0.1% by weight |
| Remainder | 0.8% by weight |

The following result was achieved:

| | |
|---|---|
| STY [t/m³/h] | 1.4 |
| Conversion | 35.7% |
| Selectivity | 86.7% |
| B | 15.59 |
| 3-Methylbutanal | 18.4% by weight |
| 2-Methylbutanal | 39.4% by weight |
| Alcohol | 0.4% by weight |
| Acid | 6.2% by weight |
| 2-Isopropyl-4-methylhexenal | 6.2% by weight |
| 2-Isopropyl-5-methylhexenal | 28.0% by weight |
| Aldol addition products | 2.1% by weight |
| Trimers | 1.5% by weight |
| Remainder | 1.2% by weight |

Example 12

This example describes the process of the invention for the co-aldol condensation of 2-MBA and 3-MBA to give an isodecenal consisting of the isomers 2-isopropyl4-methylhexenal (2+3) and 2-isopropyl-5-methylhexenal (3+3) using the cosolvent diethylene glycol (DEG). 400 kg/h of catalyst were passed through the reactor (as described in Example 3) at a temperature of 110° C. at the autogenous pressure of the reactants.

| Catalyst | |
|---|---|
| NaOH | 3.45% by weight |
| Diethylene glycol | 50.00% by weight |
| Water | 46.55% by weight |
| Starting material flow [l/h] | 4.14 |
| Starting material composition | |
| 3-Methylbutanal | 47.6% by weight |
| 2-Methylbutanal | 51.6% by weight |
| Acid | 0.6% by weight |
| Remainder | 0.3% by weight |

The following result was achieved:

| | |
|---|---|
| STY [t/m³/h] | 2.4 |
| Conversion | 63.1% |
| Selectivity | 91.0% |
| B | 14.04 |
| 3-Methylbutanal | 3.1% by weight |
| 2-Methylbutanal | 28.7% by weight |
| Alcohol | 1.5% by weight |
| Acid | 1.2% by weight |

-continued

| | |
|---|---|
| 2-Isopropyl-4-methylhexenal | 27.0% by weight |
| 2-Isopropyl-5-methylhexenal | 34.0% by weight |
| Aldol addition products | 0.6% by weight |
| Trimers | 2.5% by weight |
| Remainder | 1.4% by weight |

Example 13

This example describes the process of the invention for the co-aldol condensation of n-pentanal, 2-MBA and 3-MBA to give an isodecenal consisting of the isomers 2-propylheptenal (1+1), 2-propyl-4-methylhexenal (1+2), 2-isopropylheptenal (1+3), isopropyl-4-methylhexenal (2+3) and 2-isopropyl-5-methylhexenal (3+3). 400 kg/h of catalyst were passed through the reactor (as described in Example 3) at a temperature of 110° C. at the autogenous pressure of the reactants.

| Catalyst | |
|---|---|
| NaOH | 2.62% by weight |
| Water | 97.38% by weight |
| Starting material flow [l/h] | 3.97 |
| Starting material composition | |
| 3-Methylbutanal | 27.7% by weight |
| 2-Methylbutanal | 35.3% by weight |
| n-Pentanal | 34.8% by weight |
| Acid | 0.4% by weight |
| Aldols | 0.7% by weight |
| Remainder | 1.1% by weight |

The following result was achieved:

| | |
|---|---|
| STY [t/m³/h] | 2.5 |
| Conversion | 62.8% |
| Selectivity | 97.3% |
| B | 15.19 |
| 3-Methylbutanal | 7.4% by weight |
| 2-Methylbutanal | 22.5% by weight |
| n-Pentanal | 1.6% by weight |
| unreacted n-pentanal | |
| Alcohol | 0.2% by weight |
| Acid | 0.4% by weight |
| 2-Isopropyl-4-methylhexenal | 2.2% by weight |
| 2-Isopropyl-5-methylhexenal | 7.3% by weight |
| 2-Propyl-4-methylhexenal | 10.4% by weight |
| 2-Isopropylheptenal | 31.1% by weight |
| 2-Propylheptenal | 13.9% by weight |
| Aldol addition products | 1.7% by weight |
| Trimers | 0.6% by weight |
| Remainder | 0.7% by weight |

Example 14

This example describes the process of the invention for the co-aldol condensation of n-pentanal, 2-MBA and 3-MBA to give an isodecenal consisting of the isomers 2-propylheptenal (1 +1), 2-propyl4-methylhexenal (1+2), 2-isopropylheptenal (1+3), isopropyl-4methylhexenal (2+3) and 2-isopropyl-5-methylhexenal (3+3) using the cosolvent diethylene glycol (DEG). 400 kg/h of catalyst were passed through the reactor (as described in Example 3) at a temperature of 110° C. at the autogenous pressure of the reactants.

| Catalyst | |
|---|---|
| NaOH | 3.50% by weight |
| Diethylene glycol | 50.00% by weight |
| Water | 46.50% by weight |
| Starting material flow [l/h] | 4.11 |
| 3-Methylbutanal | 33.0% by weight |
| 2-Methylbutanal | 32.0% by weight |
| n-Pentanal | 31.8% by weight |
| Acid | 0.9% by weight |
| Aldols | 1.0% by weight |
| Trimers | 0.4% by weight |
| Remainder | 0.9% by weight |

The following result was achieved:

| | |
|---|---|
| STY [t/m³/h] | 3.3 |
| Conversion | 80.0% |
| Selectivity | 98.1% |
| B | 14.01 |
| 3-Methylbutanal | 1.9% by weight |
| 2-Methylbutanal | 13.9% by weight |
| n-Pentanal | 0.1% by weight |
| (unreacted n-pentanal) | |
| Alcohol | 1.1% by weight |
| 2-Isopropyl-4-methylhexenal | 8.9% by weight |
| 2-Isopropyl-5-methylhexenal | 12.9% by weight |
| 2-Propyl-4-methylhexenal | 18.6% by weight |
| 2-Isopropylheptenal | 29.4% by weight |
| 2-Propylheptenal | 9.8% by weight |
| Aldol addition products | 0.8% by weight |
| Trimers | 0.8% by weight |
| Remainder | 2.0% by weight |

Obviously, numerous modifications and variations of the present invention are possible in light of the above teachings. It is therefore to be understood that within the scope of the appended claims, the invention may be practiced otherwise than as specifically described herein.

What is claimed is:

1. A process for the catalytic aldol condensation of an aldehyde, comprising forming a multiphase reaction mixture in a tube reactor, said mixture comprising at least one continuous phase and at lease one phase dispersed in said continuous phase; and carrying out said aldol condensation of the aldehyde in the presence of a catalyst;

wherein the catalyst is present in the continuous phase and at least one aldehyde is present in the dispersed phase; and wherein the loading factor B of the tube reactor is equal to or greater than 0.8.

2. The process according to claim 1, wherein the aldehyde contains from 1 to 15 carbon atoms.

3. The process according to claim 1, wherein only one aldehyde is used.

4. The process according to claim 3, wherein said aldehyde is selected from the group consisting of acetaldehyde, propanal, n-butyradehyde, n-valeraldehyde, 3-methylbutyraldehyde, n-hexanal, 3-methylpetanal, 4-methylpentanal, n-heptanal, n-octanal, n-nonanal and n-decanal.

5. The process according to claim 1, wherein a mixture of two or more aldehydes having the same number of carbon atoms are used.

6. The process according to claim 1, wherein a mixture of two or more aldehydes having a different number of carbon atoms are used.

7. The process according to claim 1, wherein the continuous phase consists substantially of water.

8. The process according to claim 1, wherein the continuous phase consists substantially of water and a water-soluble organic solvent.

9. The process according to claim 8, wherein the water-soluble organic solvent is selected from the group consisting of propanediol, glycerol, diethylene glycol and dimethylformamide.

10. The process according to claim 1, wherein the catalyst used is a water-soluble basic compound.

11. The process according to claim 10, wherein the water-soluble catalyst is a hydroxide, hydrogencarbonate, carbonate, carboxylate or a mixture thereof in the form of their alkali metal or alkaline earth metal compounds.

12. The process according to claim 1, wherein the catalyst is present in the continuous phase in concentrations of from 0.1 to 15% by weight.

13. The process according to claim 1, wherein the loading factor B is greater than or equal to 0.9.

14. The process according to claim 1, wherein the loading factor B is greater than or equal to 1.0.

15. The process according to claim 1, wherein the weight ratio of the continuous phase to the dispersed phase or dispersed phases is greater than 2.

16. The process according to claim 1, wherein at least one phase containing an aldehyde is dispersed, by the energy introduced into the tube reactor, in the continuous phase.

17. The process according to claim 1, wherein said process is carried out at 30° C. to 200° C.

18. The process according to claim 1, wherein said process is carried out at 60° C. to 150° C.

19. A method of preparing a saturated alcohol, comprising hydrogenating an aldol condensation product prepared according to claim 1.

20. A method of preparing a saturated carboxylic acid, comprising preparing an aldol condensation product according to claim 1, selectively hydrogenating said product and subsequently oxidizing said product.

* * * * *